(12) United States Patent
Takano

(10) Patent No.: US 7,537,562 B2
(45) Date of Patent: May 26, 2009

(54) ENDOSCOPE APPARATUS

(75) Inventor: Masayuki Takano, Saitama (JP)

(73) Assignees: Fujinon Corporation, Saitama-shi (JP); SRJ Corporation, Tochigi (JP)

(*) Notice: Subject to any disclaimer, the term of this patent is extended or adjusted under 35 U.S.C. 154(b) by 498 days.

(21) Appl. No.: 11/044,057

(22) Filed: Jan. 28, 2005

(65) Prior Publication Data
US 2005/0165273 A1    Jul. 28, 2005

(30) Foreign Application Priority Data
Jan. 28, 2004    (JP)    ............... 2004-020027

(51) Int. Cl.
- A61B 1/00    (2006.01)
- A61M 37/00    (2006.01)
- A61M 29/00    (2006.01)

(52) U.S. Cl. .............. 600/114; 604/103.03; 604/104

(58) Field of Classification Search .......... 600/101, 600/106, 114, 115, 116, 125, 129, 130, 148, 600/154; 604/27, 34, 43, 48, 500, 506–510, 604/75, 89, 91, 95.04, 96.01, 101.01, 101.03, 604/101.04, 102.01, 103, 103.03, 103.05, 604/104, 105, 107, 164.06, 164.07, 164.11, 604/165.01, 166.01, 167.05, 167.06
See application file for complete search history.

(56) References Cited

U.S. PATENT DOCUMENTS

| | | | |
|---|---|---|---|
| 2,813,531 A | 11/1957 | Lee | |
| 3,746,003 A | 7/1973 | Blake et al. | |
| 3,913,565 A * | 10/1975 | Kawahara | 600/585 |
| 4,040,413 A | 8/1977 | Ohshiro | |
| 4,147,169 A | 4/1979 | Taylor | |
| 4,737,142 A * | 4/1988 | Heckele | 604/95.04 |
| 5,512,051 A | 4/1996 | Wang et al. | |
| 5,540,711 A * | 7/1996 | Kieturakis et al. | 606/192 |
| 5,779,624 A | 7/1998 | Chang | |
| 5,971,990 A * | 10/1999 | Venturelli | 623/1.11 |
| 6,346,092 B1 | 2/2002 | Leschinsky | |
| 6,375,637 B1 | 4/2002 | Campbell et al. | |
| 6,723,113 B1 * | 4/2004 | Shkolnik | 606/194 |
| 2001/0044597 A1 | 11/2001 | Maki et al. | |
| 2002/0062119 A1 | 5/2002 | Zadno-Azizi | |
| 2002/0082639 A1 | 6/2002 | Broome et al. | |
| 2004/0073162 A1 * | 4/2004 | Bleam et al. | 604/103 |

FOREIGN PATENT DOCUMENTS

| | | |
|---|---|---|
| EP | 1 254 679 | 11/2002 |
| JP | 64-20832 | 1/1989 |
| JP | 01020832 | 1/1989 |

(Continued)

Primary Examiner—Linda C Dvorak
Assistant Examiner—Alireza Nia
(74) Attorney, Agent, or Firm—Young & Thompson

(57) ABSTRACT

An endoscope apparatus, comprising:
an endoscope with a balloon attached to a tip end part of an insertion section, and
an insertion assisting tool into which the insertion section of the endoscope is inserted and which assists the insertion section in being inserted into a body cavity,
wherein a tip end part of the insertion assisting tool is constructed to have a diameter enlarging structure capable of being enlarged in diameter, and by enlarging a diameter of the tip end part, a balloon of the insertion section protruded from a tip end of the insertion assisting tool is made extractable from the insertion assisting tool.

2 Claims, 13 Drawing Sheets

FOREIGN PATENT DOCUMENTS

| | | |
|---|---|---|
| JP | 6-75404 | 10/1994 |
| JP | 10-248794 | 9/1998 |
| JP | 11-178786 | 7/1999 |
| JP | 11-290324 | 10/1999 |
| JP | 2000-126122 | 5/2000 |
| JP | 2001-340462 | 12/2001 |
| JP | 2002-301019 | 10/2002 |
| JP | 2002-532131 | 10/2002 |
| WO | WO 03/101523 | 12/2003 |

* cited by examiner

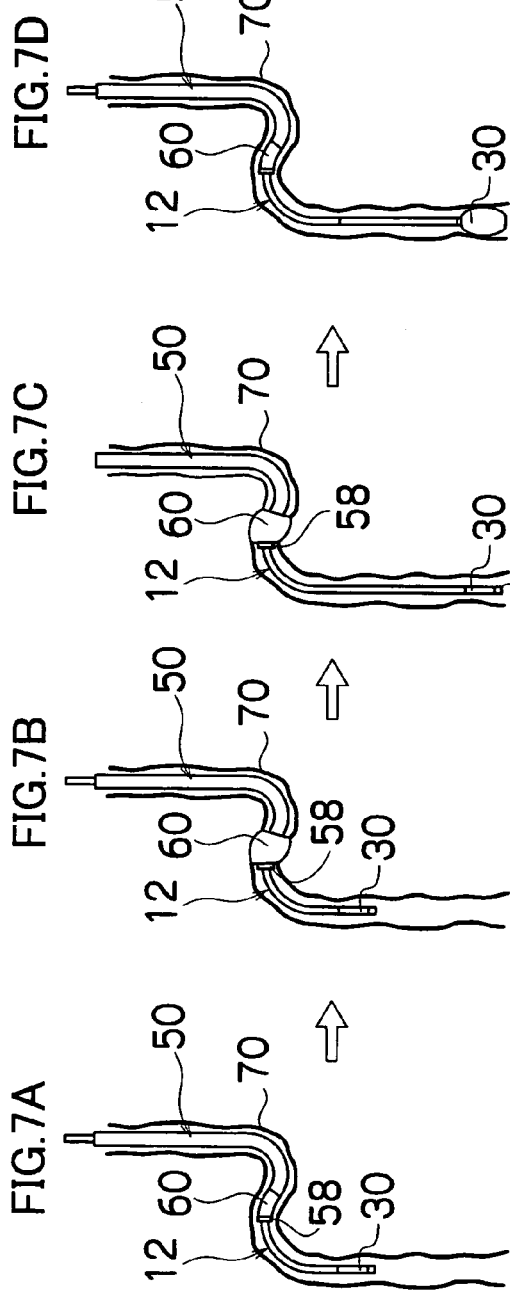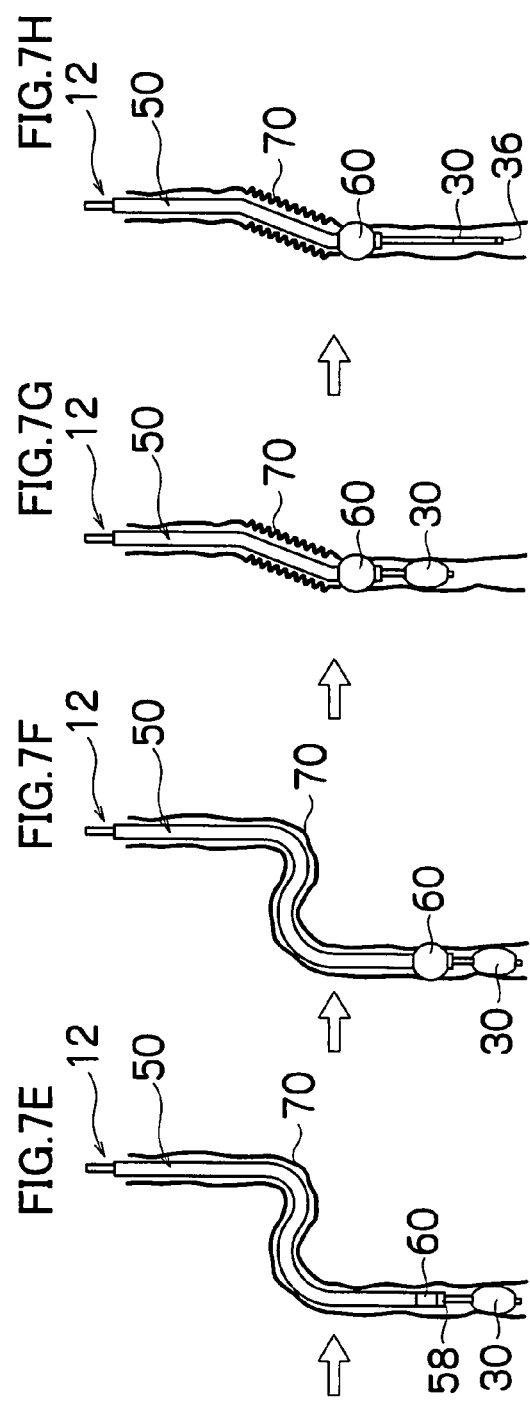

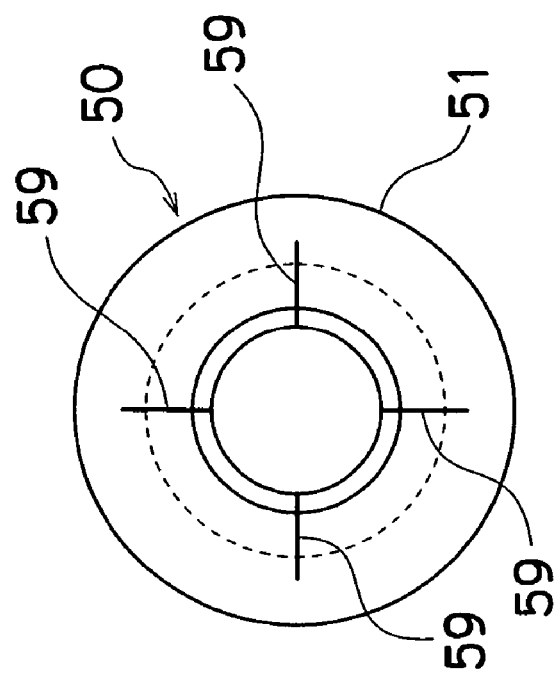
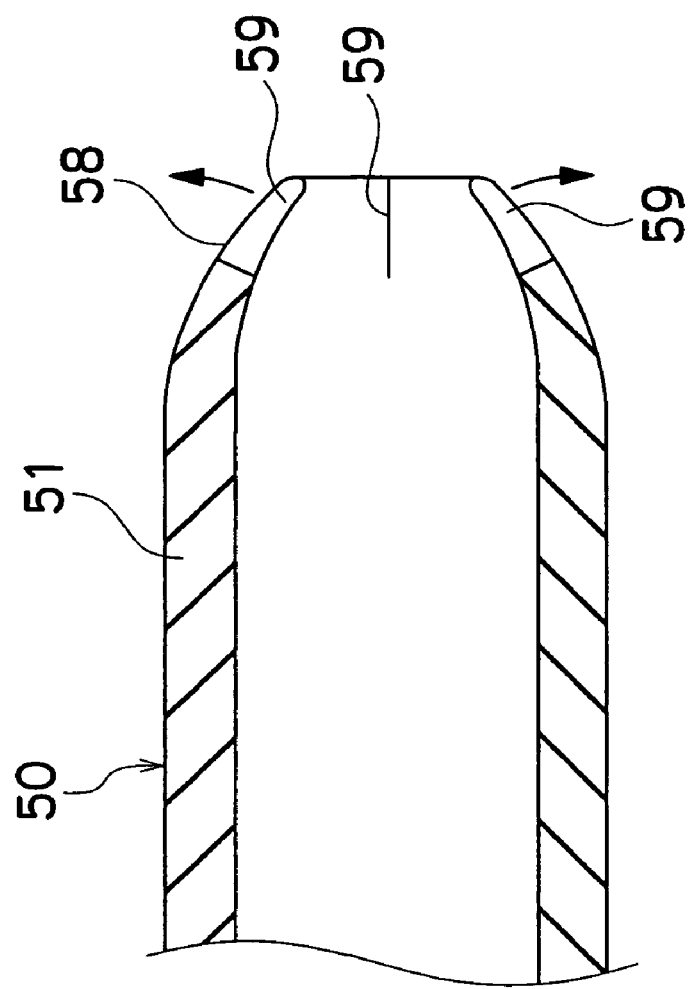
FIG.8A
FIG.8B

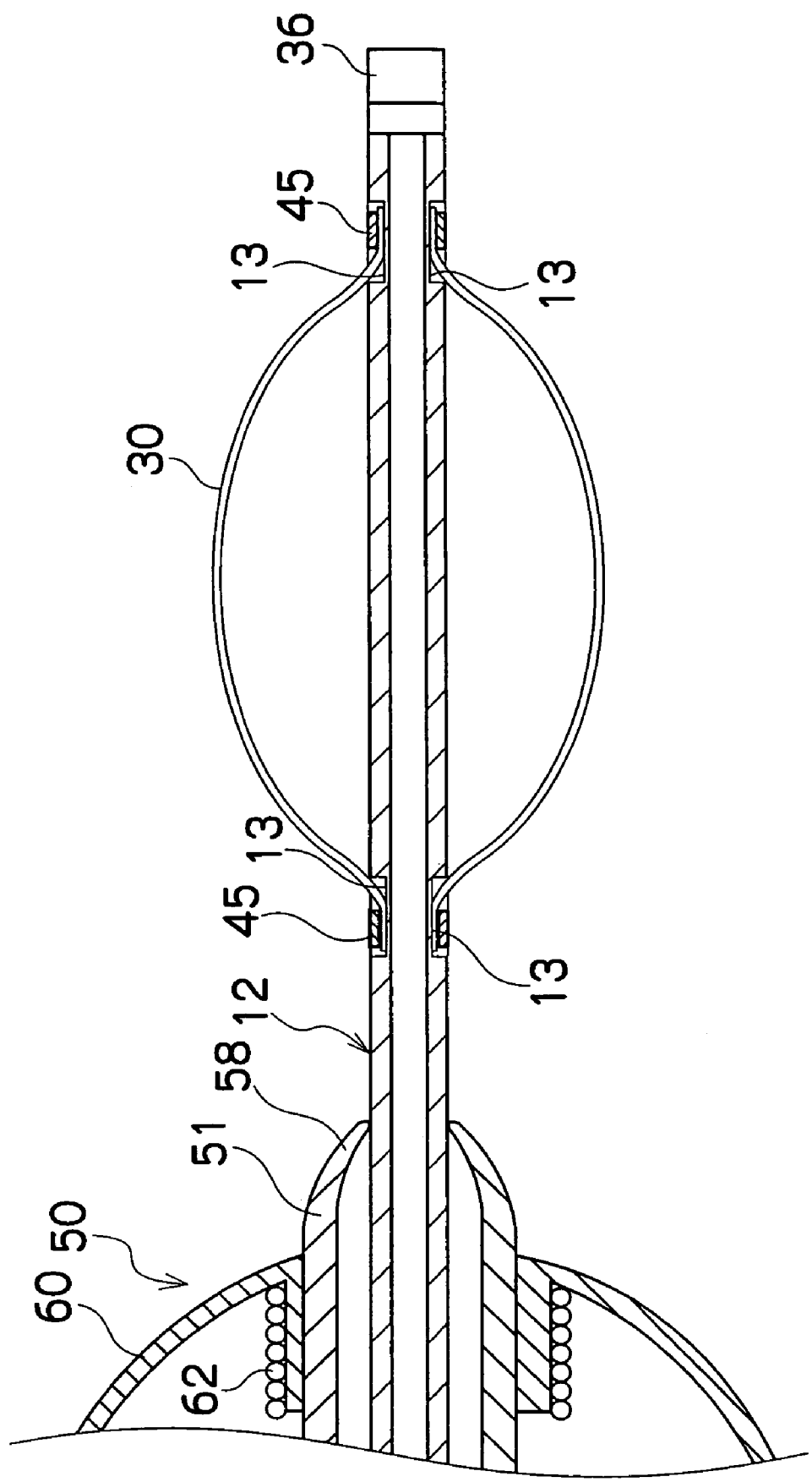

ENDOSCOPE APPARATUS

BACKGROUND OF THE INVENTION

1. Field of the Invention

The present invention relates to an endoscope apparatus, and more particularly, to an endoscope apparatus having an endoscope with a balloon attached to a tip end of an insertion section, and an insertion assisting tool for guiding the insertion section of the endoscope into a body cavity.

2. Description of the Related Art

When the insertion section of an endoscope is inserted into a deep alimentary canal such as a small intestine, by only pushing the insertion section into the deep alimentary canal, the force is difficult to transmit to a tip end of the insertion section due to complicated bending of an intestinal canal, and insertion into a deep part is difficult. Thus, there is proposed an endoscope apparatus which prevents excessive bending and deflection of the insertion section by inserting the insertion section into a body cavity with an insertion assisting tool called an over tube or a sliding tube attached to the insertion section of the endoscope, and guiding the insertion section with this insertion assisting tool (for example, Japanese Patent Application Laid Open No. 10-248794).

In conventional endoscope apparatuses, there is known a double balloon type endoscope apparatus provided with a balloon at a tip end part of an endoscope insertion section and provided with a balloon at a tip end part of an insertion assisting tool (for example, Japanese Patent Application Laid Open No. 2001-340462 and Japanese Patent Application Laid Open No. 2002-301019).

Incidentally, as the procedure of the endoscope apparatus using an insertion assisting tool, a desired procedure is desired to be performed by inserting a treatment tool such as a balloon dilator for widening a narrow region of an intestinal canal and a contrast tube for injecting a contrast medium for observing the narrow region of the intestinal canal. However, these treatment tools are objects with comparatively large diameters, and therefore, they cannot be inserted by using a forceps channel inserted and disposed in the endoscope insertion section. Therefore, it has been desired to extract only the endoscope insertion section with the insertion assisting tool left in the body cavity and insert these treatment tools with the insertion assisting tool as a guide.

SUMMARY OF THE INVENTION

However, the tip end part of the insertion assisting tool has a tip end formed into a throttled shape to prevent an intestinal wall from being entangled or pinched as disclosed in Japanese Patent Application Laid Open No. 2001-340462, and therefore, the balloon of the endoscope insertion section is caught by the tip end part of the insertion assisting tool when the endoscope insertion section is extracted, and it is difficult to extract the endoscope insertion section from the insertion assisting tool.

The present invention is made in view of the above circumstances, and has its object to provide an endoscope apparatus in which an endoscope insertion section with a balloon attached to a tip end of the insertion section is capable of being extracted from an insertion assisting tool.

In order to attain the above-described object, a first aspect of the present invention is in an endoscope apparatus comprising an endoscope with a balloon attached to a tip end part of an insertion section, and an insertion assisting tool into which the insertion section of the endoscope is inserted and which assists insertion section in being inserted into a body cavity, characterized in that a tip end part of the insertion assisting tool is constructed to have a diameter enlarging structure capable of being enlarged in diameter, and by enlarging a diameter of the tip end part, a balloon of the insertion section protruded from a tip end of the insertion assisting tool is made extractable from the insertion assisting tool.

According to the first aspect of the present invention, the tip end part of the insertion assisting tool is constructed to have the diameter enlarging structure, and therefore, the insertion section having the balloon which is protruded from the tip end of the insertion assisting tool can be easily extracted from the insertion assisting tool.

According to a second aspect of the present invention, the diameter enlarging structure is characterized by being made capable of being enlarged in diameter by constructing the tip end part of the insertion assisting tool by a soft member. Namely, a soft member such as rubber, sponge or the like is used for the material of only the throttled portion of the tip end part of the insertion assisting tool, whereby the tip end part is easily enlarged in diameter, and therefore, the insertion section having the balloon protruded from the tip end of the insertion assisting tool can be easily extracted from the insertion assisting tool.

According to a third aspect of the present invention, in order to attain the aforementioned object, the diameter enlarging structure is characterized by being made capable of being enlarged in diameter by forming a notch in the tip end part of the insertion assisting tool. By enhancing flexibility by forming a notch in the throttled portion of the tip end part of the insertion assisting tool, the tip end part is easily enlarged in diameter, and therefore, the balloon can be easily extracted.

A fourth aspect of the present invention is in an endoscope apparatus comprising an endoscope with a balloon attached to a tip end part of an insertion section by a catching member, and an insertion assisting tool into which the insertion section of the endoscope is inserted and which assists the insertion section in being inserted into a body cavity, characterized in that a surface of the catching member is formed into an inclined surface toward a downstream side from an upstream side in an extracting direction of the insertion section with respect to the insertion assisting tool, and thereby, the balloon of the insertion section protruded from the tip end of the insertion assisting tool is made extractable from the insertion assisting tool. The surface of the catching member is formed into the inclined surface of which height becomes larger toward the downstream side from the upstream side in the extracting direction, and the balloon is made extractable from the insertion assisting tool. Namely, when the insertion section is pulled in the extracting direction, the tip end of the insertion assisting tool rides on the inclined surface of the catching member and the balloon sinks inside the tip end part, and therefore, the insertion section can be easily extracted from the insertion assisting tool.

In order to attain the aforesaid object, a fifth aspect of the present invention is in an endoscope apparatus comprising an endoscope with a balloon attached to a tip end part of an insertion section by a catching member, and an insertion assisting tool into which the insertion section of the endoscope is inserted and which assists the insertion section in being inserted into a body cavity, characterized in that the catching member and an outer peripheral surface of the insertion section are made substantially flush with each other by fitting the catching member in a recessed part formed in the outer peripheral surface of the insertion section, and thereby, the balloon of the insertion section protruded from the tip end of the insertion assisting tool is made extractable from the insertion assisting tool. When the insertion section is pulled in the extracting direction, the tip end part of the insertion assisting tool does not collide against the catching member which interferes with the extraction, and therefore, the insertion section can be easily extracted from the insertion assisting tool. By forming the recessed part in the outer peripheral surface of the insertion section to which the catching member is fitted, the outer diameter of the insertion section does not become thick after fitting of the catching member, and the recessed part also serves as the mark of the balloon attaching position.

According to the present invention, the tip end part of the insertion assisting tool is constructed to have the diameter enlarging structure, and therefore, the balloon of the insertion section protruded from the tip end of the insertion assisting tool can be easily extracted from the insertion assisting tool.

BRIEF DESCRIPTION OF THE DRAWINGS

FIGS. 7A to 7H are explanatory views showing an operation method of the endoscope apparatus shown in FIG. 1;

FIGS. 8A to 8B are explanatory views showing a second embodiment in which the diameter enlarging structure is given to the over tube side;

FIG. 14 is an enlarged sectional view of an essential part showing the second embodiment in which the diameter enlarging structure is given to the insertion section side.

DETAILED DESCRIPTION OF THE PREFERRED EMBODIMENTS

Hereinafter, preferred embodiments of an endoscope apparatus according to the present invention will be explained in accordance with the attached drawings.

Figure 1:
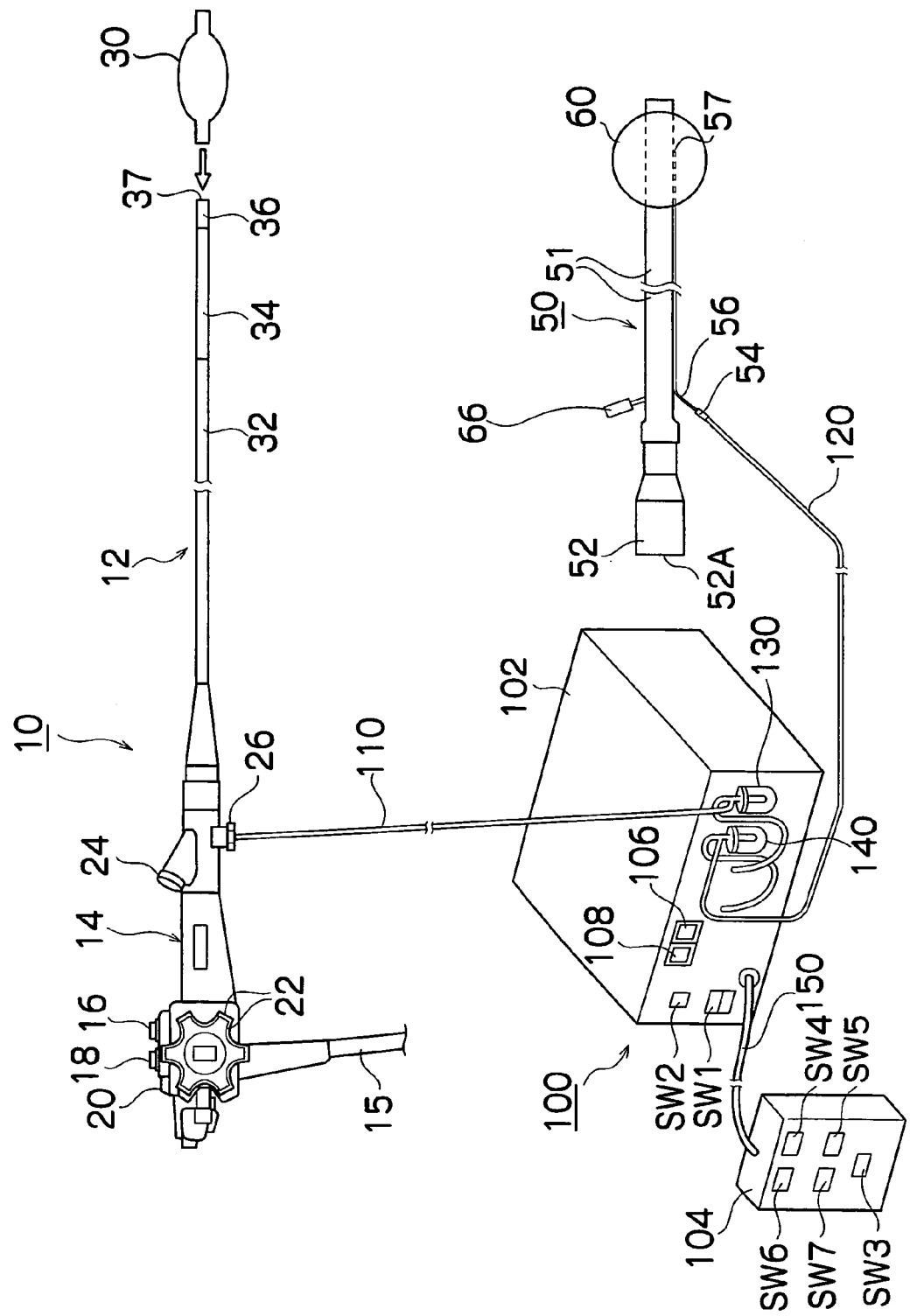
FIG. 1 is a system schematic diagram of an endoscope apparatus according to an embodiment of the present invention.

FIG. 1 shows a system block diagram of an endoscope apparatus according to the embodiments of the present invention. The endoscope apparatus shown in the drawing is constructed by an endoscope 10, an over tube (corresponding to an insertion assisting tool) 50, and a balloon control device 100.

The endoscope 10 includes a hand operation section 14, and an insertion section 12 connected to the hand operation section 14. A universal cable 15 is connected to the hand operation section 14, and a connecter (not shown) which is connected to a processor and a light source device not shown is provided at a tip end of the universal cable 15.

An air/water passing button 16, a suction button 18, and a shutter button 20 which are operated by an operator are provided in parallel on the hand operation section 14, and a pair of angle knobs 22 and 22, and the forceps insertion part 24 are provided respectively at predetermined positions. Further, the hand operation section 14 is provided with a balloon air port 26 for supplying air to a first balloon 30 and sucking air from the balloon 30.

The insertion section 12 is constructed by a flexible part 32, a curving part 34 and a tip end rigid part 36. The curving part 34 is constructed by connecting a plurality of node rings to be able to curve, and is remotely operated to curve by the rotational operation of a pair of angle knobs 22 and 22 provided on the hand operation section 14. Thereby, a tip end surface 37 of the tip end part 36 can be faced in a desired direction.

Figure 2:
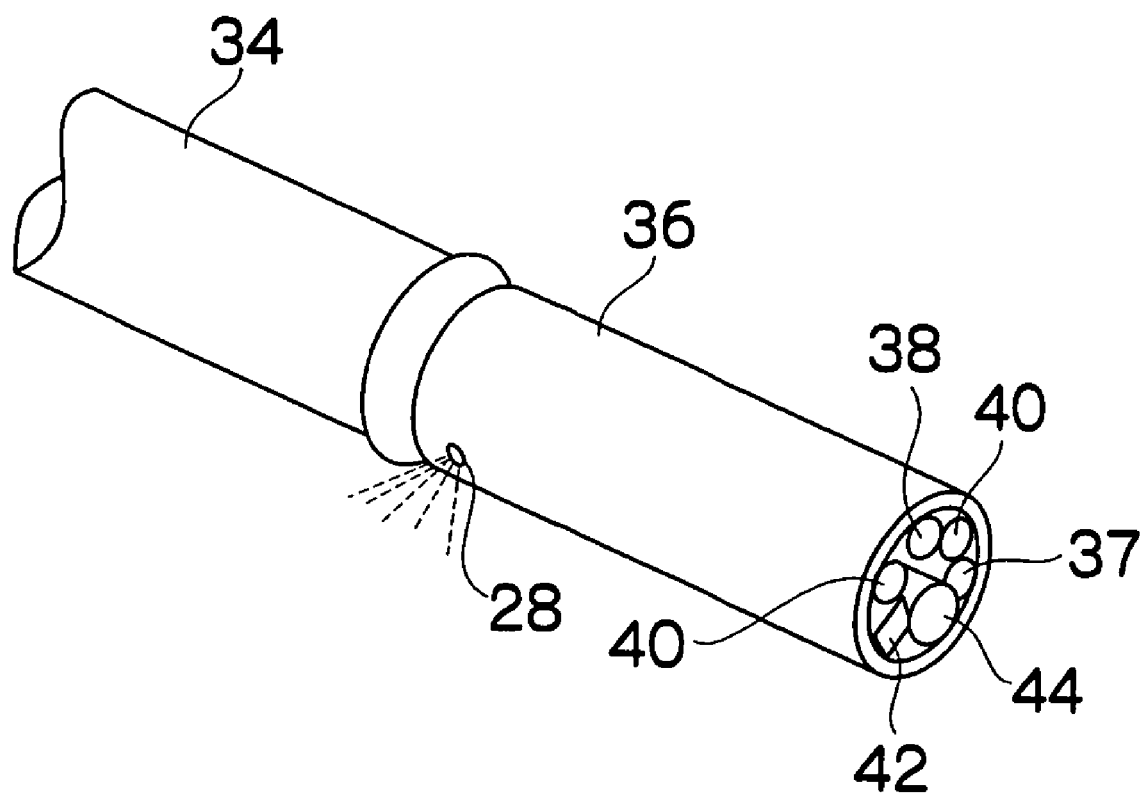
FIG. 2 is a perspective view showing a tip end part of an insertion section of an endoscope.

As shown in FIG. 2, the tip end surface 37 of the tip end part 36 is provided with an object optical system 38, an illumination lens 40, air/water passing nozzle 42, a forceps port 44 and the like in predetermined positions. An air supply/suction port 28 is provided on an outer peripheral surface of the tip end part 36, and this air supply/suction port 28 communicates with the balloon air port 26 in FIG. 1 via an air supply tube (not shown) with an inner diameter of about 0.8 mm which is inserted into the insertion section 12. Accordingly, air is blown out of the air supply/suction port 28 of the tip end part 36 by supplying air to the balloon air port 26, and on the other hand, air is sucked from the air supply/suction port 28 by sucking air from the balloon air port 26.

Figure 3:
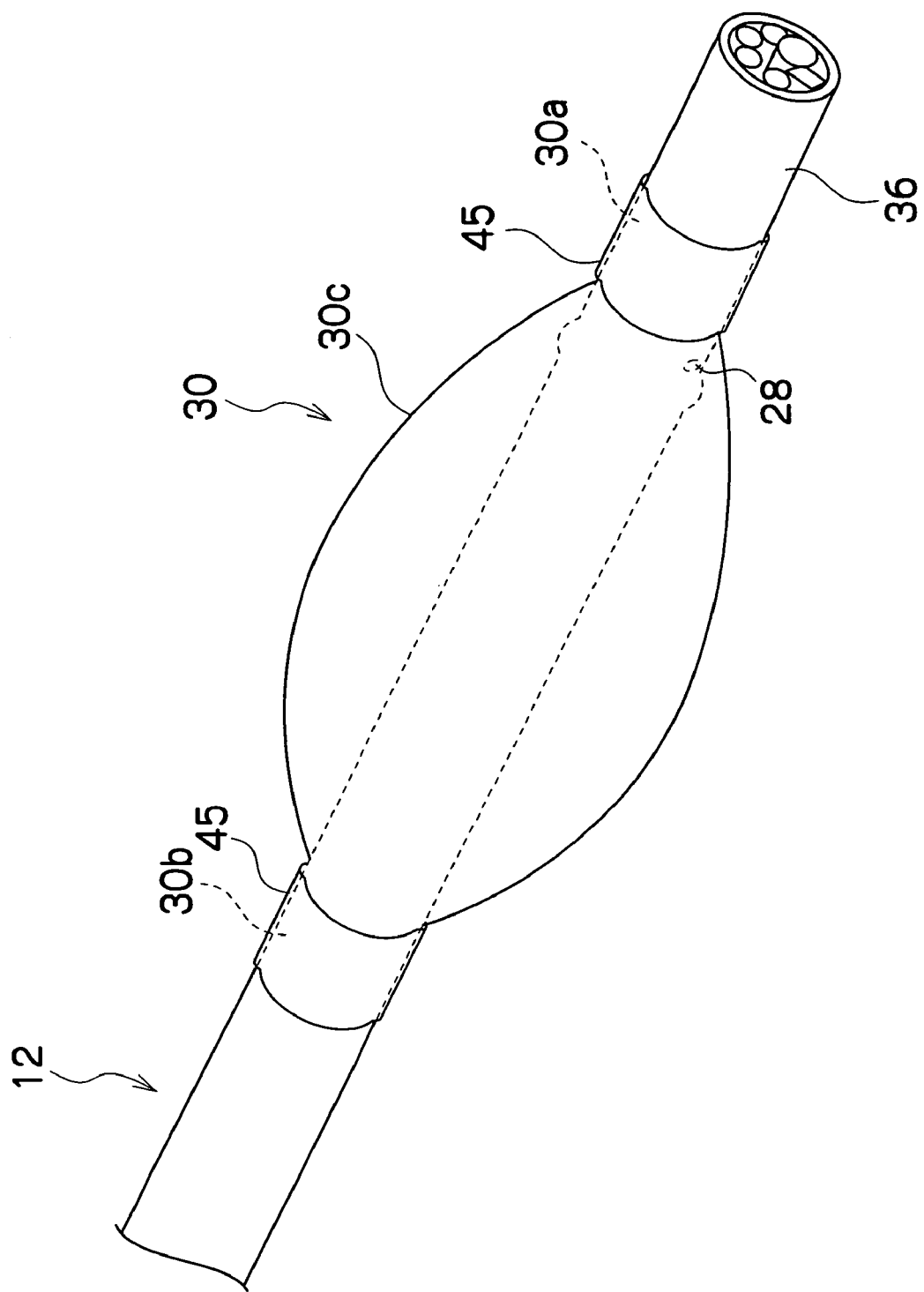
FIG. 3 is a perspective view showing the tip end rigid part of the insertion section onto which a first balloon is fitted.

As shown in FIG. 1, the first balloon 30 constituted of an elastic body such as rubber is detachably attached to the tip end part 36 of the insertion section 12. The fist balloon 30 is formed by a bulging portion 30c in a center and attaching portions 30a and 30b at both ends of the bulging portion 30c, and is attached to the tip end rigid part 36 side so that the air supply/suction port 28 is located inside the bulging portion 30c, as shown in FIG. 3. The attaching portions 30a and 30b are formed to have smaller diameters than the diameter of the tip end part 36, and after being closely fitted onto the tip end part 36 with their elastic forces, the attaching portions 30a and 30b are firmly fitted to an outer peripheral surface of the tip end part 36 by ring-shaped bands (catching members) 45 and 45 shown in FIGS. 4 and 5.

The first balloon 30 fitted onto the tip end part 36 has its bulging portion 30c inflated in a substantially spherical shape by air supplied from the air supply/suction port 28 shown in FIG. 2. On the other hand, by sucking air from the air supply/suction port 28, the bulging portion 30c is deflated and is closely fitted onto the outer peripheral surface of the tip end part 36.

Figure 4:
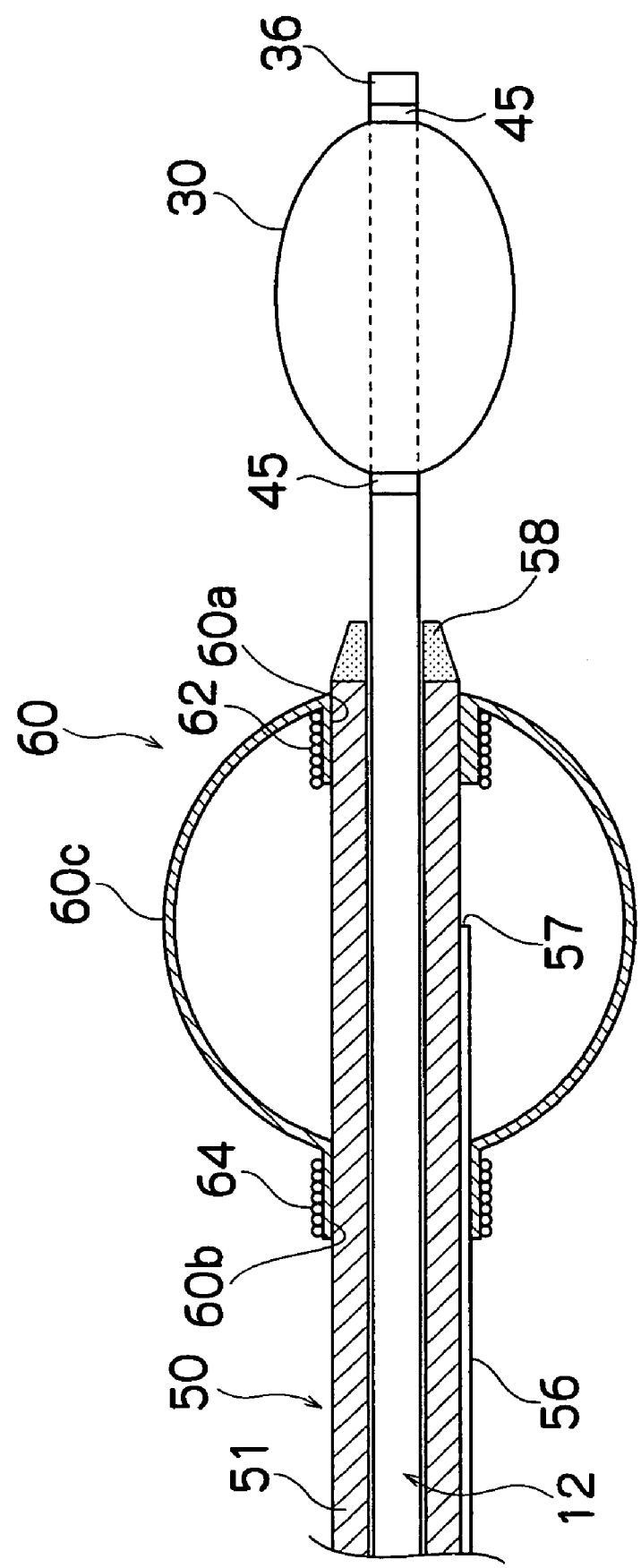
FIG. 4 is a sectional side view showing a tip end part of an over tube through which the insertion section is inserted.

The over tube 50 shown in FIG. 1 is constructed by a tube body 51, and a gripping part 52. The tube body 51 is formed into a cylindrical shape as shown in FIG. 4, and has a slightly larger inner diameter than an outer diameter of the insertion section 12. The tube body 51 is a molded product of flexible urethane resin, with its outer peripheral surface covered with lubricating coat and with its inner peripheral surface also covered with the lubricating coat. The rigid gripping part 52 is fitted in the tube body 51 in a watertight state, and the gripping part 52 is connected to the tube body 51 to be detachable and attachable. The insertion section 12 is inserted toward the tube body 51 from a base end opening 52A of the gripping part 52.

A balloon air port 54 is provided at the base end side of the tube body 51 as shown in FIG. 1. An air supply tube 56 with an inner diameter of about 1 mm is connected to the balloon air port 54, and this tube 56 is bonded to an outer peripheral surface of the tube body 51 and is provided to extend to a tip end portion of the tube body 51 as shown in FIG. 4.

A tip end 58 of the tube body 51 is formed into a tapered shape to prevent the intestinal wall from being entangled or the like. A second balloon 60 constituted of an elastic body such as rubber is fitted onto the base end side of the tip end part 58 of the tube body 51. The second balloon 60 is fitted in the state in which the tube body 51 penetrates through the balloon 60, and is constructed by a bulging portion 60c in a center, and attaching portions 60a and 60b at both ends of the bulging portion 60c. The attaching portion 60a at the tip end side is folded back to the inside of the bulging portion 60c, and the attaching portion 60a folded back is fixed to the tube body 51 with an X-ray contrast thread 62 wound around the attaching portion 60a. The attaching portion 60b at the base end side is disposed outside the second balloon 60, and is fixed to the tube body 51 with a thread 64 wound around the attaching portion 60b.

The bulging portion 60c is formed into a substantially spherical shape in a natural state (the state in which the bulging portion 60c does not inflate or deflate), and as for the size, the bulging portion 60c is formed to be larger than the size of the first balloon 30 in a natural state (the state in which the balloon 30 does not inflate or deflate). Accordingly, when the air is supplied to the first balloon 30 and the second balloon 60 at the same pressure, the outer diameter of the bulging portion 60c of the second balloon 60 becomes larger than the outer diameter of the bulging portion 30c of the first balloon 30. The outer diameter of the second balloon 60 is constructed so as to be ϕ50 mm when the outer diameter of the first balloon 30 is ϕ25 mm, for example.

The aforementioned tube 56 is opened in the inside of the bulging portion 60c, and an air supply/suction port 57 is formed. Accordingly, when air is supplied from the balloon air port 54, the air is blown from the air supply/suction port 57 and thereby, the bulging portion 60c is inflated. When air is sucked from the balloon air port 54, the air is sucked from the air supply/suction port 57, and the second balloon 60 is deflated.

Figure 5:
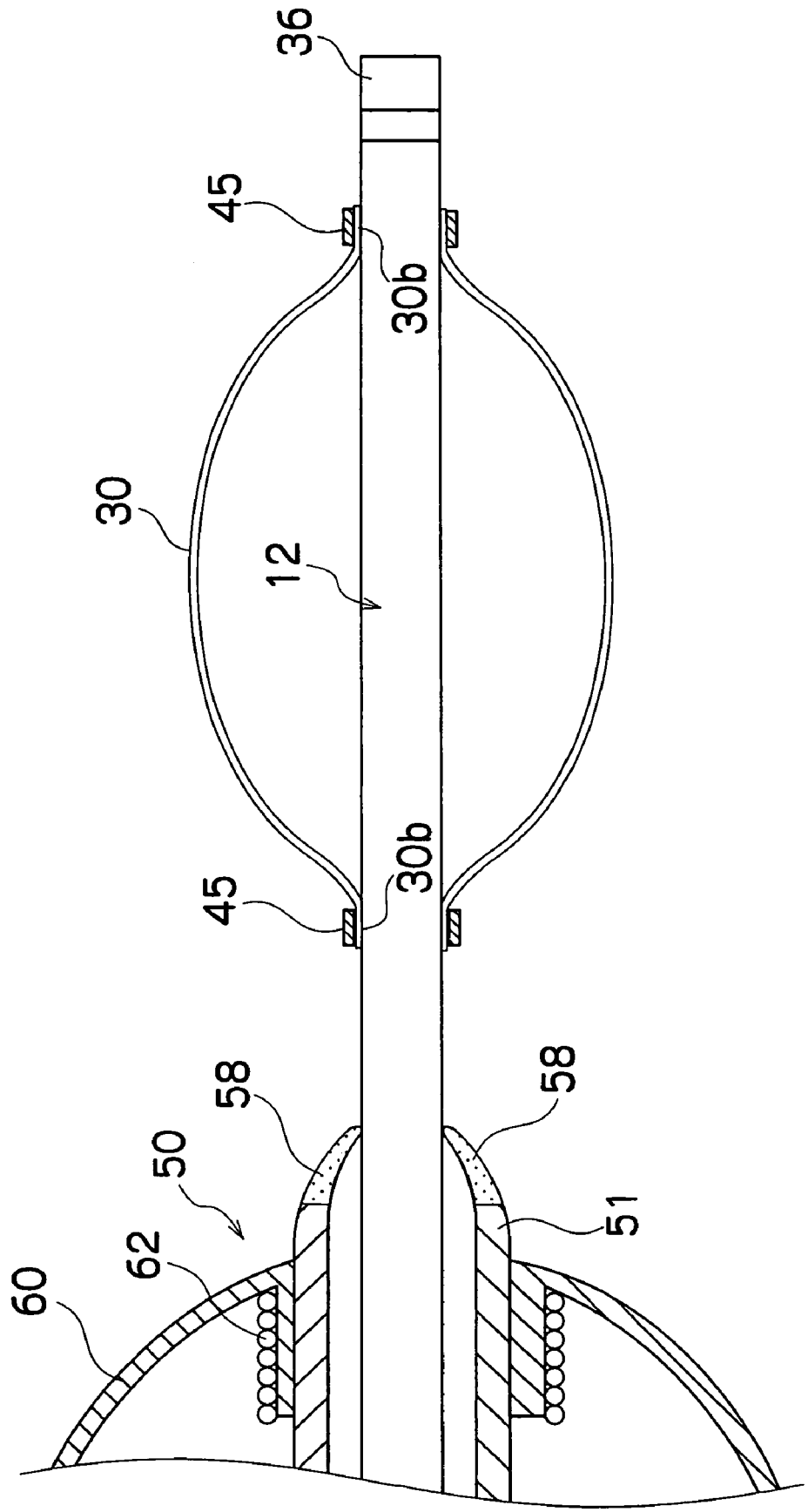
FIG. 5 is an enlarged sectional view of an essential part showing a first embodiment in which a diameter enlarging structure is given to the over tube side.
Figure 6:
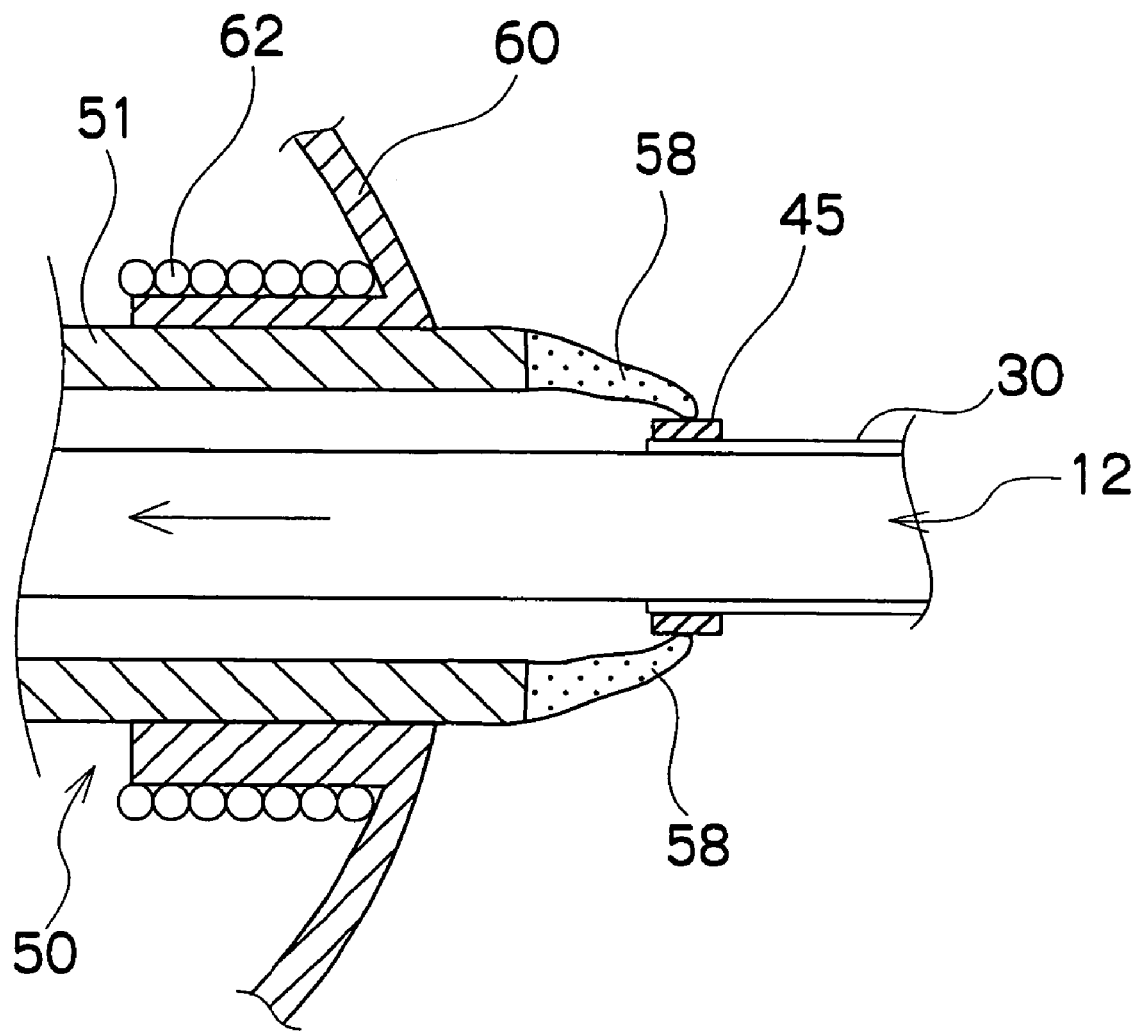
FIG. 6 is an explanatory view showing an insertion section extracting situation by the diameter enlarging structure shown in FIG. 5.

Incidentally, the tip end part 58 of the tube body 51 is made of a sponge which is a soft member as shown in FIG. 5. This sponge tip end part 58 is formed into a tubular shape with a narrowed tip, but is elastically deformed easily by the pressing operation by the bands 45 and enlarged in diameter when the endoscope insertion section 12 is extracted from the tube body 51 as shown in FIG. 6.

Meanwhile, the balloon control device 100 in FIG. 1 is the device which supplies and sucks fluid such as air to and from the first balloon 30, and supplies and sucks fluid such as air to and from the second balloon 60. The balloon control device 100 is constructed by a device body 102 including a pump, sequencer and the like not shown, and a hand switch 104 for remote control.

A front panel of the device body 102 is provided with a power supply switch SW1, a stop switch SW2, a pressure gauge 106 for the first balloon 30 and a pressure gauge 108 for the second balloon 60. A tube 110 for supplying/sucking air to and from the first balloon 30, and a tube 120 for supplying/sucking air to and from the second balloon 60 are attached to the front panel of the device body 102. Liquid storing tanks 130 and 140 for storing body fluid, which flows backward from the first balloon 30 and the second balloon 60 when the first balloon 30 and the second balloon 60 are broken, are respectively provided at midpoints of the respective tubes 110 and 120.

Meanwhile, the hand switch 104 is provided with a similar stop switch SW3 to the stop switch SW2 at the side of the device body 102, an ON/OFF switch SW4 for supporting pressurization/decompression of the first balloon 30, a pose switch SW5 for keeping the pressure of the first balloon 30, an ON/OFF switch SW6 for supporting pressurization/decompression of the second balloon 60, and a pose switch SW7 for keeping the pressure of the second balloon 60. This hand switch 104 is electrically connected to the device body 102 via a cable 150.

The balloon control device 100 which is constructed as above supplies air to the first balloon 30 and the second balloon 60 and inflates the first balloon 30 and the second balloon 60, and controls the air pressure at a fixed value to keep the first balloon 30 and the second balloon 60 in the inflated state. The balloon control device 100 sucks air from the first balloon 30 and the second balloon 60 and deflates the first balloon 30 and the second balloon 60, and controls the air pressure at a fixed value to keep the first balloon 30 and the second balloon 60 in the deflated state.

Next, an operation method of the endoscope apparatus will be explained in accordance with FIGS. 7A to 7H.

First, as shown in FIG. 7A, the insertion section 12 is inserted into an intestinal canal (for example, descending limb of duodenum) 70 in the state in which the over tube 50 covers the insertion section 12. At this time, the first balloon 30 and the second balloon 60 are deflated.

Next, as shown in FIG. 7B, in the state in which the tip end 58 of the over tube 50 is inserted into a bent portion of the intestinal canal 70, air is supplied to the second balloon 60 to inflate the second balloon 60. As a result, the second balloon 60 is caught by the intestinal canal 70, and the tip end 58 of the over tube 50 is fixed at the intestinal canal 70.

Next, as shown in FIG. 7C, only the insertion section 12 of the endoscope 10 is inserted into a deep part of the intestinal canal 70. Then, as shown in FIG. 7D, air is supplied to the first balloon 30 to inflate the first balloon 30. As a result, the first balloon 30 is fixed at the intestinal canal 70. In this case, the first balloon 30 is smaller in size at the time of inflation than the second balloon 60, and therefore, the burden exerted on the intestinal canal 70 is small, thus making it possible to prevent damage to the intestinal canal 70.

Next, after air is sucked from the second balloon 60 to deflate the second balloon 60, the over tube 50 is pushed in, and inserted along the insertion section 12, as shown in FIG. 7E. Then, after the tip end 58 of the over tube 50 is pushed into the vicinity of the first balloon 30, air is supplied to the second balloon 60 to inflate the second balloon 60 as shown in FIG. 7F. As a result, the second balloon 60 is fixed at the intestinal canal 70. Namely, the intestinal canal 70 is gripped by the second balloon 60.

Next, as shown in FIG. 7G, the over tube 50 is drawn in. Thereby, the intestinal canal 70 contracts substantially straight, and excessive deflection and bending of the over tube 50 are eliminated. When the over tube 50 is drawn in, both the first balloon 30 and the second balloon 60 are caught by the intestinal canal 70, but the friction resistance of the first balloon 30 is smaller than the friction resistance of the second balloon 60. Therefore, even if the first balloon 30 and the second balloon 60 move to relatively separate from each other, the first balloon 30 with small friction resistance slides with respect to the intestinal canal 70, and therefore, it does not happen that the intestinal canal 70 is damaged by being pulled by both the balloons 30 and 60.

Next, as shown in FIG. 7H, air is sucked from the first balloon 30 to deflate the first balloon 30. Then, the tip end part 36 of the insertion section 12 is inserted into as deep a part of the intestinal canal 70 as possible. Namely, the inserting operation as shown in FIG. 7C is performed again. Thereby, the tip end part 36 of the insertion section 12 can be inserted into a deep part of the intestinal canal 70. When the insertion section 12 is further inserted into a deep part, the pushing operation as shown in FIG. 7E is performed after the fixing operation as shown in FIG. 7D is performed, the gripping operation as shown in FIG. 7F and the drawing operation as shown in FIG. 7G, and the inserting operation as shown in FIG. 7H are repeatedly performed in sequence. Thus, the insertion section 12 can be further inserted into a deep part of the intestinal canal 70.

Next, when the over tube 50 is retained at a target region of the intestinal canal 70 and only the insertion section 12 is extracted from the over tube 50, air is extracted from the first balloon 30 in the first place and thereby, the first balloon is deflated. Thereafter, when the over tube 50 is fixed and the insertion section 12 is extracted, the band 45 collides against the sponge tip end part 58 as shown in FIG. 6, and the sponge tip end part 58 is easily deformed by that force and enlarged in diameter. As a result, the band 45 and the first balloon 30 easily pass through the sponge tip end part 58, and the insertion section 12 is easily extracted from the over tube 50. In this manner, the insertion section 12 having the first balloon 30 protruded from the tip end of the over tube 50 can be easily extracted from the over tube 50 by giving the diameter enlarging structure in which the tip end part 58 is made of a sponge. The soft member such as rubber may be applied in place of the sponge.

FIGS. 8A and 8B show another embodiment in which the tip end part 58 of the over tube 50 is constructed to be in a diameter enlarging structure, and according to the drawings, notches 59, 59 . . . are provided in the tip end part 58 to facilitate elastic deformation of the tip end part 58 in the diameter enlarging direction. The notches 59 are formed at four locations equidistantly around the tip end part 58, and are formed along an axial direction of the over tube 50. Thus, when the band 45 shown in FIG. 6 collides against the tip end part 58 in FIG. 8, the tip end part 58 receives the force in the extracting direction of the insertion section 12, and is elastically deformed in the diameter enlarging direction shown by the arrow in FIG. 8A to allow passage of the band 45 and the first balloon 30. As a result, the insertion section 12 can be easily extracted from the over tube 50.

Figure 9:
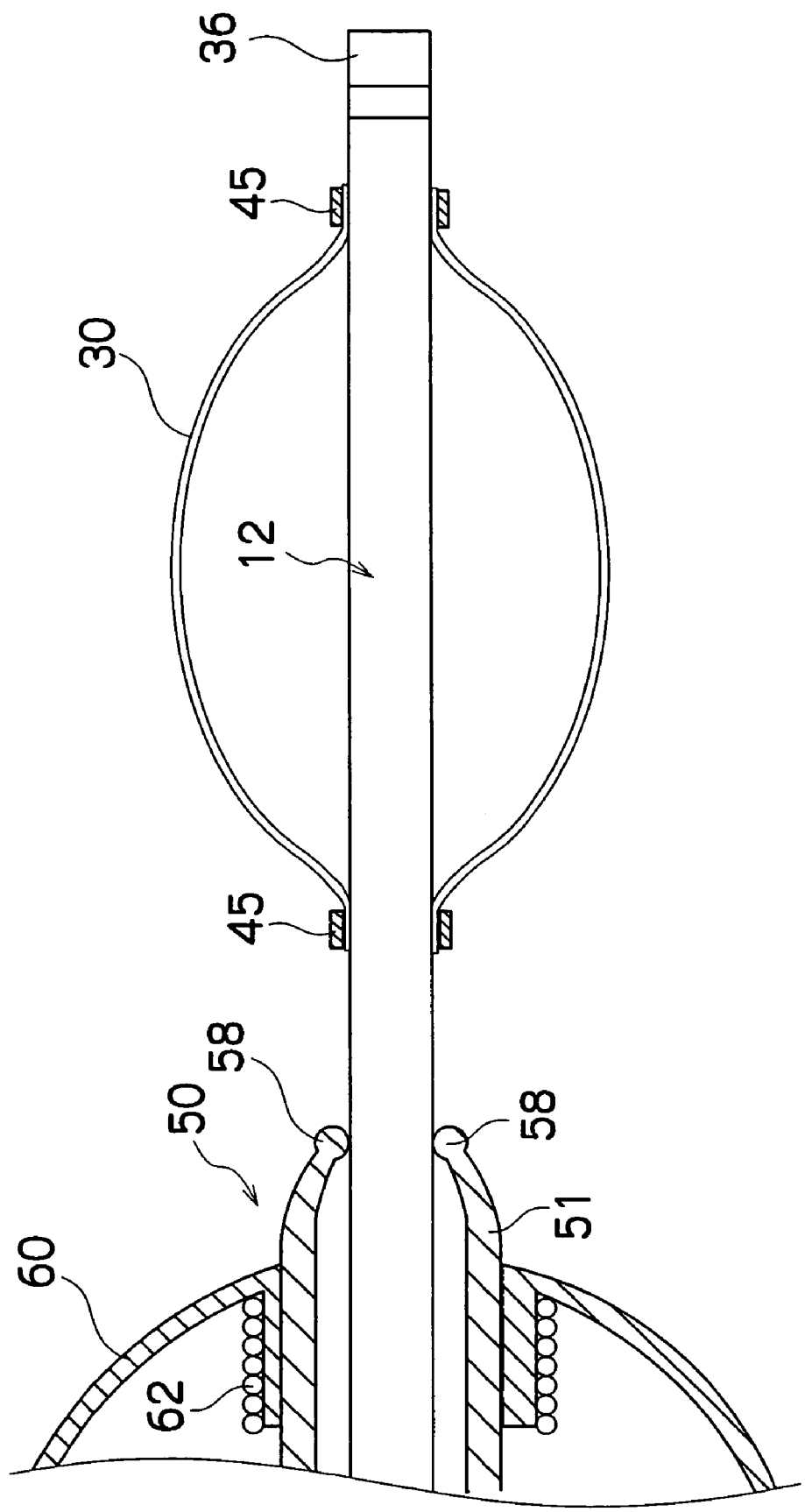
FIG. 9 is an enlarged sectional view of an essential part showing a third embodiment in which the diameter enlarging structure is given to the over tube side.
Figure 10:
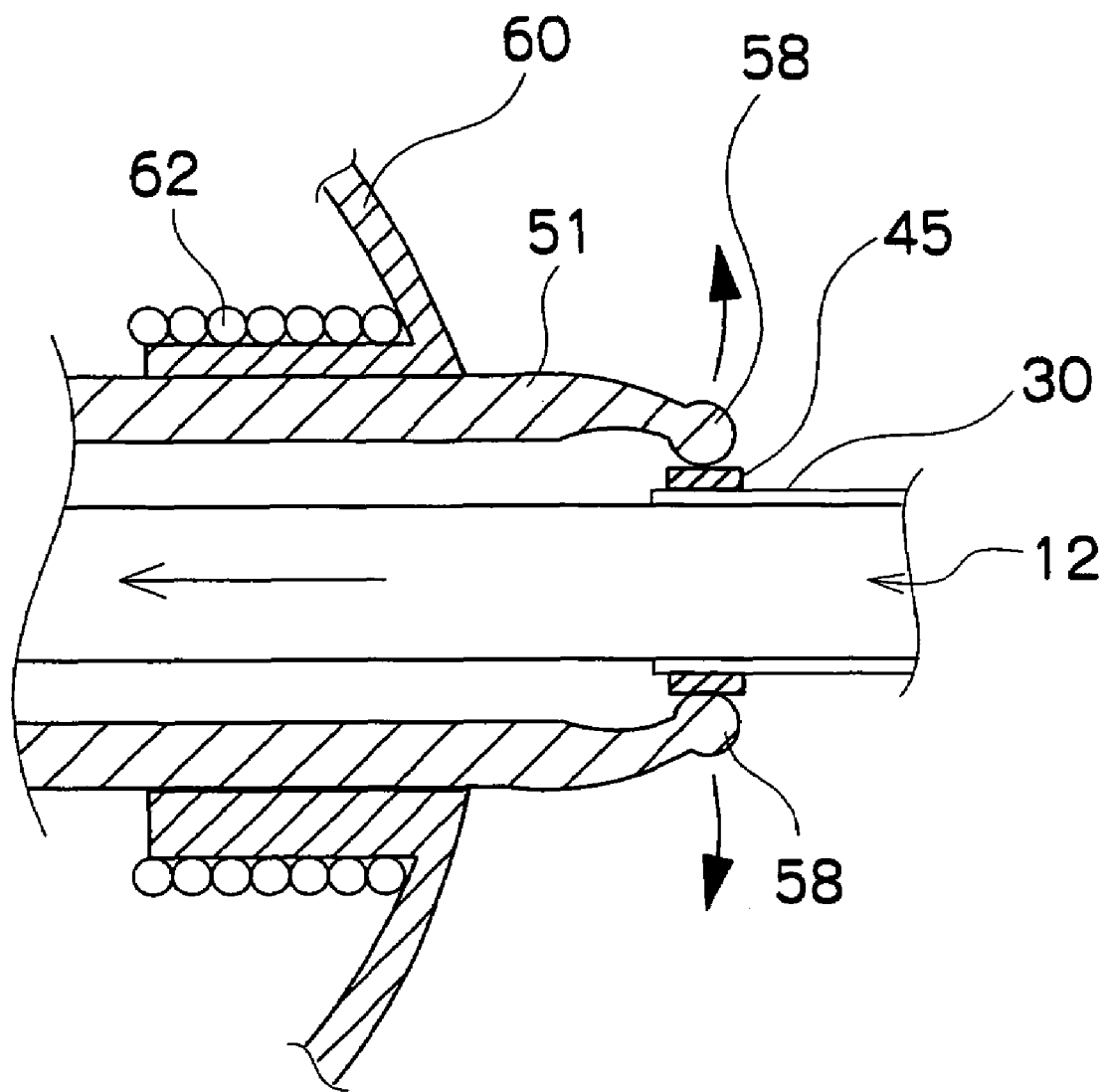
FIG. 10 is an explanatory view showing an insertion section extracting situation by the diameter enlarging structure shown in FIG. 9.

FIG. 9 is another embodiment in which the tip end part 58 of the over tube 50 is constructed to have the diameter enlarging structure, and according to the drawing, the tip end part 58 is formed in a circular shape in section. Thereby, when the band 45 collides against the tip end part 58 and the force in the extracting direction acts on the tip end part 58 from the band 45, the band 45 sinks into an inside of the tip end part 58 by being guided by the circular surface of the tip end part 58, and the tip end part 58 is easily elastically deformed in the diameter enlarging direction shown by the arrow in FIG. 10 by the force. As a result, the tip end part 58 allows the passage of the band 45 and the first balloon 30. Thereby, the insertion section 12 can be easily extracted from the over tube 50.

Figure 11:
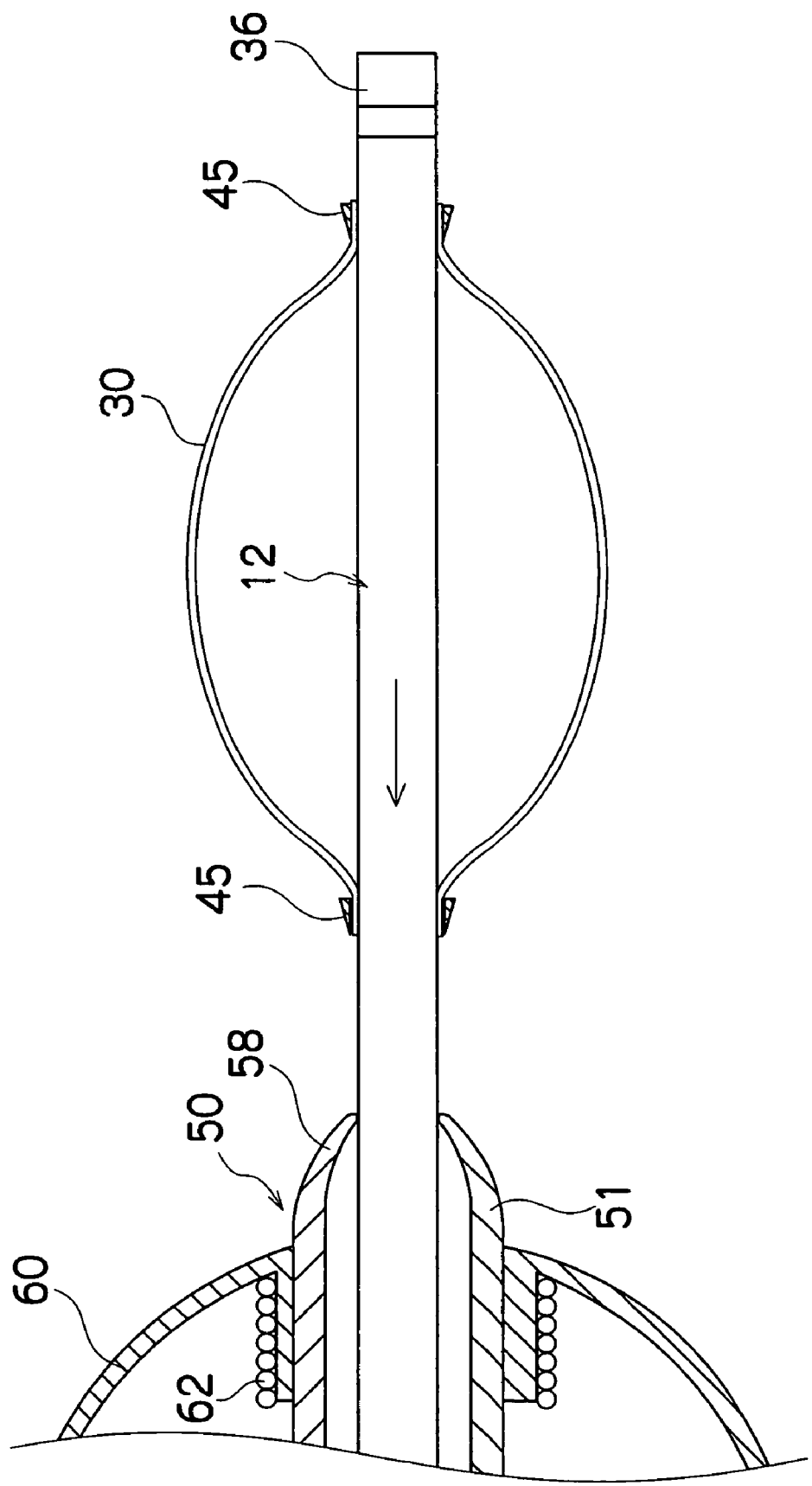
FIG. 11 is an enlarged sectional view of an essential part showing the first embodiment in which the diameter enlarging structure is given to the insertion section side.
Figure 12:
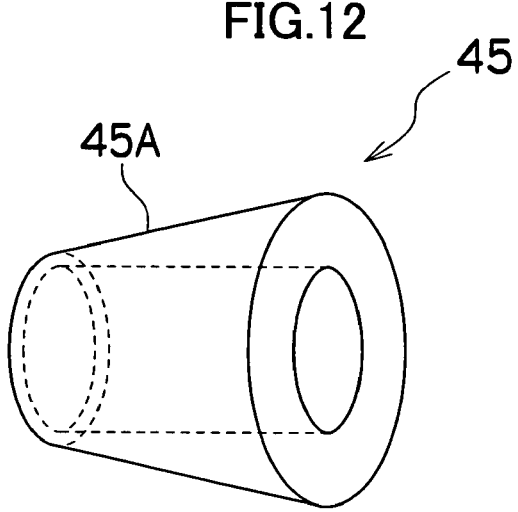
FIG. 12 is an enlarged perspective view of a band shown in FIG. 11.
Figure 13:
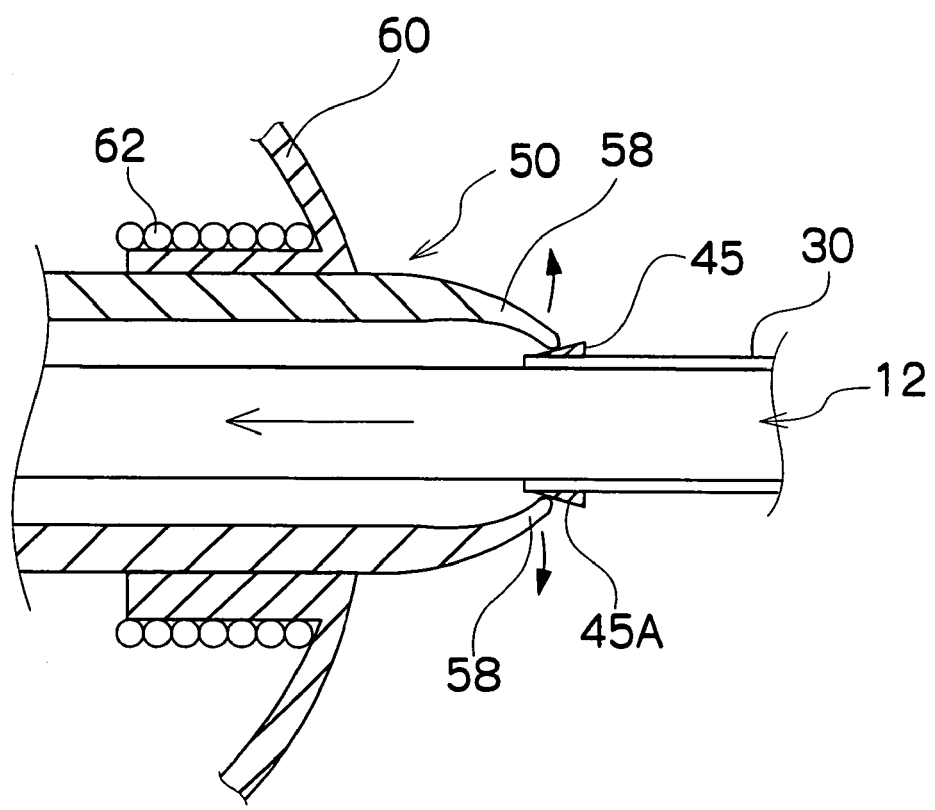
FIG. 13 is an explanatory view showing an insertion section extracting situation by the diameter enlarging structure shown in FIG. 11.

FIG. 11 is an embodiment in which the band 45 for fitting the first balloon 30 onto the insertion section 12 is improved, and as shown in FIGS. 11 and 12, the surface of the band 45 is formed into an inclined plane 45A of which height becomes larger from an upstream side in the extracting direction toward a downstream side, whereby it is made easy for the tip end part 58 of the over tube 50 to ride over the band 45 and the first balloon 30. Namely, when the band 45 collides against the tip end part 58 and the force in the extracting direction acts on the tip end part 58 from the band 45 as shown in FIG. 13, the band 45 sinks into the inside of the tip end part 58 with the inclined surface 45A as a guide, and the tip end part 58 elastically deforms in the diameter enlarging direction shown by the arrow in FIG. 13 by the force. As a result, the tip end part 58 allows passage of the band 45 and the first balloon 30. Thereby, the insertion section 12 can be easily extracted from the over tube 50.

FIG. 14 is an embodiment in which the insertion section 12 is improved, recessed parts 13 and 13 are formed at the band fitting positions of the outer peripheral surface of the insertion section 12, and the band 45 is fitted in the recessed parts 13 and 13, whereby the bands 45 and 45 and the outer peripheral surface of the insertion section 12 are made substantially flush with each other. Thereby, the band 45 passes through the tip end part 58 without colliding against the tip end part 58, and therefore, the insertion section 12 can be easily extracted from the over tube 50. By forming the recessed parts 13 in the insertion section 12, the outer diameter of the insertion section 12 does not become large after the band 45 is fitted thereto, and the recessed parts 13 also serves as the marks of the balloon attaching position.

In the embodiments, the over tube having the balloon 50 at the tip end is explained as the insertion assisting tool, but the insertion assisting tool is not limited to this, and the diameter enlarging structure of the embodiment may be applied to a sliding tube (insertion assisting tool without having a balloon) which is used for a colonoscope.

What is claimed is:

1. An endoscope apparatus, comprising:
an endoscope with a balloon attached to a tip end part of an insertion section by two annular catching members, each having an internal annular surface pressing against an external surface of a respective end of the balloon and holding the respective end of the balloon on the tip end part, and
an insertion assisting tool into which the insertion section of the endoscope is inserted and which assists the insertion section in being inserted into a body cavity,
wherein an external surface of each of the two annular catching members is an inclined surface that slants in a same direction toward a downstream side from an upstream side in an extracting direction of the insertion section with respect to the insertion assisting tool, and
wherein a height of the inclined surface becomes larger from the upstream side in the extracting direction toward the downstream side,
thereby, the balloon of the insertion section protruded from the tip end of the insertion assisting tool is made extractable from the insertion assisting tool and the tip end part of the insertion assisting tool is made to ride over the annular catching members and the balloon.

2. The endoscope apparatus of claim 1, wherein each said catching member is, in cross section, a triangle with a base generally perpendicular to an axis of the insertion section.

* * * * *